April 20, 1971 E. GRAHAM Plant Pat. 3,049
STRAWBERRY
Filed July 17, 1969
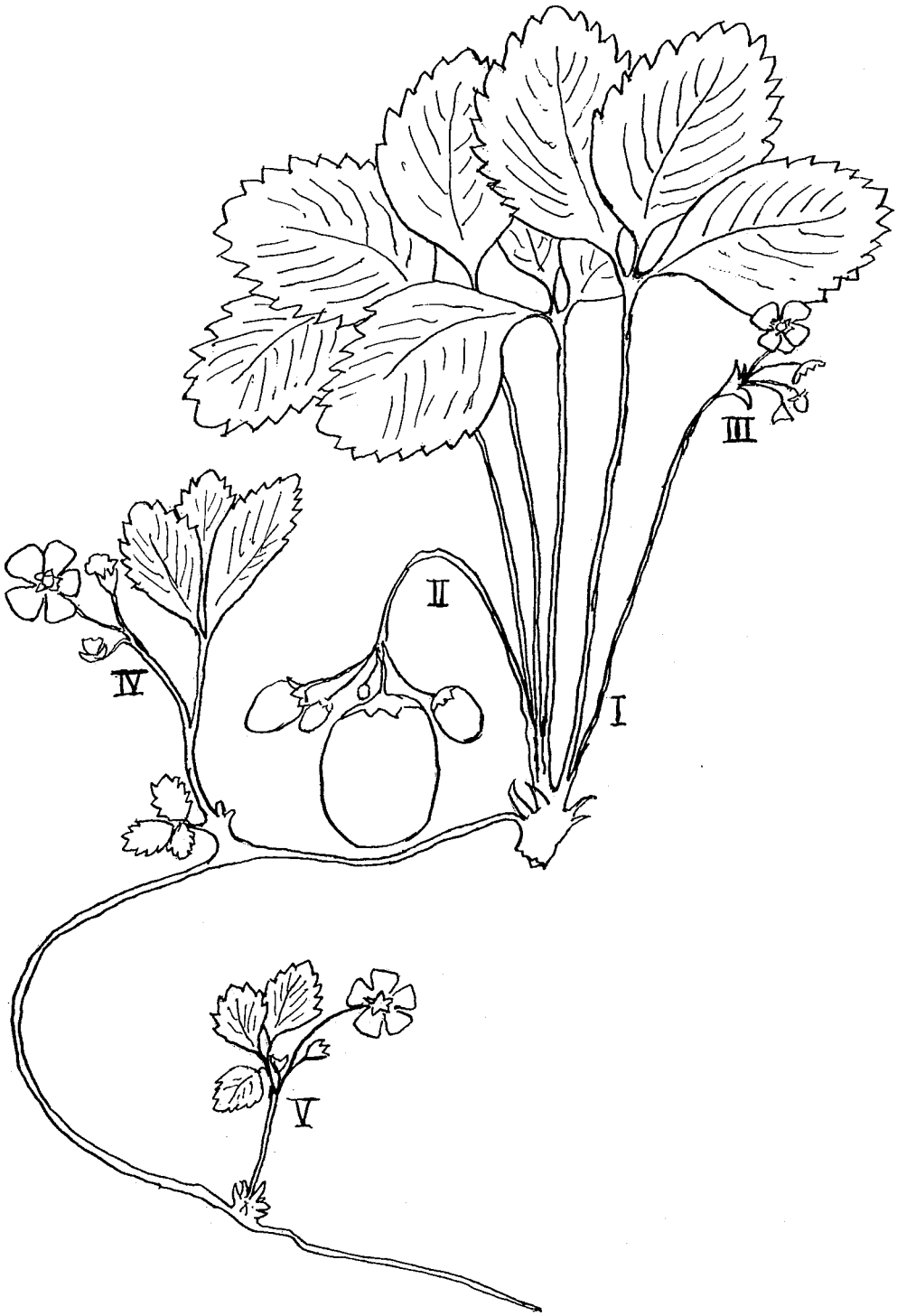
Edna Graham United States Patent Office Plant Pat. 3,049
Patented Apr. 20, 1971

3,049
STRAWBERRY

Edna Graham, One Farm, Shear Hill Road,
Mahopac, N.Y. 10541

Filed July 17, 1969, Ser. No. 842,741
Int. Cl. A01h 5/03
U.S. Cl. Plt.—49 1 Claim My invention relates to a new and distinct variety of strawberry plant especially designed and bred for the home gardener.

This strawberry is to my knowledge the only one which gives continuous production from first spring fruits until after heavy frost.

Mother plants were first produced at our "Lowridge" farm near Matteson, Ill. and subsequently at our "Old Farm" near Mahopac, N.Y.; also tested in "strawberry barrel" cultivation in the north side of Chicago. These plants have been asexually reproduced in all these locations over the past eleven years and characteristics more strongly developed over this time.

The ancestry is complex, including native Illinois wild strawberry stock crossed successively with Dunlap, Fairfax, Gem, Mastodon, Superfection, and Red Rich.

My new variety shows many characteristics of its several ancestors, the light red color of the wild berry, its truncated conical shape, the cluster habit of fruiting of the wild berry and its spreading habit, also its longevity even under adverse conditions.

In the accompanying drawings is illustrated berry, leaf, and runner plants of typical size and shape. In said drawings, FIG. 1 is the front elevation of a typical plant showing fruiting habit, shape of berry, simultaneous blossom and fruit production and runner growth.

FIG. 2 shows cluster-type fruiting habit. Special mention should be made that fruits ripen consecutively in rotation and not all at the same time. It is quite possible that it is this characteristic which contributes largely to the continuity of production.

FIG. 3 shows second fruiting stem in bloosm while first stem is developing and ripening fruits. Many plants have two or three such stems in various stages of growth at the same time.

FIG. 4 shows a typical runner plant illustrating characteristic fruit stem already in blossom even though runner plant is scarcely rooted.

FIG. 5 second runner plant also beginning to bloom while on mother plant.

I now refer more in detail to my new variety of strawberry; the plant and berry have the following distinctive characteristics which combine to distinguish them from the other known varieties:

The plant is extremely hardy, bearing after light frost and even until the ground is frozen. It is prolific in runner production and has the unique quality of producing berries on the runner plants as soon as they begin to root and sometimes without a separate root system at all.

The plants start bearing early—May or mid-June depending upon the season and bear continuously until October or, in an unusually open year even until mid-November. Example: One season in Illinois when berries were given light protection we had fresh strawberry short-cake from these strawberries from the garden on Thanksgiving day.

As a convenient summary, the following is a detailed description of this new variety of strawberry plant:

*Plant characteristics*

Size: Medium root system, relatively small plants, sparse foliage, root system comparable to Gem.

Crown size: About ¼ of an inch thick, about ¾ inch in length.

Leaves: Generally trifoliate, smaller than most berry varieties, of similar configuration to the wild strawberry. Size approximately as illustrated.

Petiole: Heavy and quite short.

Leaflets: Obovate: broader in the middle, narrower at either end than most varieties, of the general conformation of the leaflet of the wild strawberry plant, sharply indented edges.

Runners: Freely produced. Unusually prolific in runners from runner plant. It is usual for one runner to produce three runner plants along one runner stem, all of which will flower and fruit in the same season as they set. Runner plants will frequently flower and fruit even before they are rooted in soil.

Flower stems: Thick and semi-upright, generally partially exposed, slightly pubescent.

Flower: Medium to large, petal shape and set resembling wild strawberry.

Sex: Bisexual.

Fruit stems: Cluster of five to seven berries on thick upright fruit stalk. Individual berry stems thick and strong, somewhat pubescent.

Soil: Plants have been grown successfully in nearly all soil types and in perforated barrels on city balconies.

Culture: Sufficient to maintain relatively weed-free ground. Needs considerable moisture.

Disease resistance: Excellent. Has been tested for resistance to major diseases at Cornell University.

Insect resistance: Good.

Frost resistance: Good.

Drought resistance: Poor.

Rain resistance: Good.

Fruit: Condition when described—very good.

*Date described.*—August 17.

*Size.*—Varies from very large, similar to largest Mastodon, to large, to medium, depending greatly on the position of the individual berry in the fruit cluster. The first to ripen is the largest, next as large or somewhat smaller; third and fourth, medium, fifth, medium or small.

*Surface contour.*—Irregular.

*Shape.*—Conical, blunted point.

Fruit stems: Pubescent, thick, considerably longer than wild strawberry but generally of similar conformation.

Aspect: Shiny with medium red color throughout entire berry including inconspicuous core. Similar to F. Virginiana.

Seeds: Bright yellow, flush with berry surface.

Core: Long, soft-textured, almost indistinguishable in color and texture from body of berry.

Calyx: Large, flat against top of berry, light green, very slightly pubescent.

Flesh: Juicy, tender.

Flavor: Extra good, sweet, fragrant, peculiarly strawberry-like.

*Fruit*

Quality: Excellent for eating, freezing and jam and preserve making. Not fit for shipping.

Uses: This berry has been developed with only one use in mind-the home garden. The home gardener has always been faced with the problem of feast or famine in the strawberry patch. Even with the several "everbearing" varieties this is true. There are always more quarts ripe at a given time than the gardener can conveniently use and then a long interval before more come on the plants; then again a brief period of glut and a long interval of no berries. My new variety provides an even supply of berries throughout the season.

The strawberry described above and the plant producing the same may vary in slight details, depending upon the weather conditions and the soil conditions under which they are grown.

I claim:

1. An everbearing strawberry that is truly an everbearer, one that is in continuous production from first spring fruiting until plants are killed by heavy frost, characterized by its habit of successive ripening of berries on each cluster; setting and ripening of fruits on runner plants to third and fourth progression on runners; exceptional vigor and reproductiveness; exceptional weather hardiness; small plants; large berries.

No references cited.

ROBERT E. BAGWILL, Primary Examiner